(12) United States Patent
Houston et al.

(10) Patent No.: US 6,453,752 B1
(45) Date of Patent: Sep. 24, 2002

(54) FIXTURE FOR TESTING SHEAR STRENGTH IN TAILOR WELDED BLANKS

(75) Inventors: Daniel Quinn Houston, Dearborn; Peter A. Friedman, Ann Arbor; William Steven Stewart, Dearborn, all of MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/498,687

(22) Filed: Feb. 7, 2000

(51) Int. Cl.[7] ............................................... G01N 3/20
(52) U.S. Cl. ........................................ 73/850; 73/841
(58) Field of Search ..................... 73/850, 856, 841, 73/862, 392, 842, 827; 219/121.63; 72/21.4

(56) References Cited

U.S. PATENT DOCUMENTS 5,415,047 A * 5/1995 Maciejewski et al. ........ 73/850
5,591,360 A * 1/1997 Mombo-Caristan .... 219/121.64
5,736,645 A    4/1998 Chin-Chan et al.

* cited by examiner

Primary Examiner—Max Noori
(74) Attorney, Agent, or Firm—Raymond L. Coppiellie

(57) ABSTRACT

A fixture is provided for testing the shear strength of a longitudinal weld which interconnects a plurality of planar blanks forming a tailor welded blank. The fixture includes a first pair of triangular shaped face plates connected to one side of the tailor welded blank and a second pair of triangular shaped face plates connected to the other side of the tailor welded blank. Each of the face plates includes a transverse edge which extends across the longitudinal weld connecting the planar blanks. The fixture further includes each of the transverse edges having a first portion and a second portion spaced from and parallel to the first portion. The fixture also includes an isolation portion interconnecting the first and second portions of the transverse edges adjacent the longitudinal weld for isolating a portion of the weld whereby the isolated portion of the weld is tested for shear resistance by applying a tensile load to the first and second pair of face plates.

9 Claims, 3 Drawing Sheets

FIXTURE FOR TESTING SHEAR STRENGTH IN TAILOR WELDED BLANKS

BACKGROUND OF THE INVENTION

1. Field of the Invention

The present invention relates generally to a fixture for testing the shear strength of a longitudinal weld interconnecting two or more planar blanks forming a tailor weld blank.

2. Description of the Related Art

The desire to manufacture lighter-weight and lower cost vehicles has resulted in the automotive industry looking at alternative materials, other than steel, for manufacturing vehicle body structures. Aluminum is one such material because it has qualities such as low density, good mechanical properties and high corrosion resistance. Additionally, cost and weight can be saved with aluminum vehicle body structures with the use of tailor welded blanks. Tailor welded blanks include two or more sheets of material, such as aluminum, of dissimilar thicknesses and/or material properties which are joined together through some type of welding process. Tailor welded blanks eliminate the conventional need for reinforcement parts and stamping dies used to manufacture them, thus, reducing weight and cost. Additionally, tailor welded blanks are often stiffer than conventional reinforced structures, thus making it possible to down-gauge the material used in the blanks.

Welding of steel tailor welded blanks tends to increase the strength of the weld material which helps prevent failure along the length of the weld during forming, such as stamping. Aluminum tailor welded blanks, however, do not experience this increase in strength, and therefore, may have a greater tendency to fail along the length of the weld. Additionally, the gauge, or thickness, differential intrinsic to tailor welded blanks may result in strain localization during stamping of the aluminum structures. This strain localization along the length of the weld may potentially be more severe in aluminum because of its limited formability as compared to the typical drawing-quality steels. The dominant failure mode in tailor welded blanks is shear and therefore, it is desirable to provide a method and fixture for testing the shear strength of a tailor welded blank and quickly access the feasibility of a particular tailor welded blank for an aluminum vehicle body structure.

SUMMARY OF THE INVENTION

Accordingly, the present invention is a fixture for testing the shear strength of a generally longitudinal weld interconnecting at least two planar blanks forming a tailor welded blank. The fixture includes a first pair of face plates connected to one side of the planar blanks wherein each of the first pair of face plates includes a transverse edge extending across the longitudinal weld which connects each of the planar blanks. The fixture further includes a second pair of face plates connected to the opposing side of the planar blanks wherein each of the second pair of face plates includes a transverse edge extending across the longitudinal weld which connects each of the planar blanks. The fixture includes the transverse edges of the first and second pair of face plates having a first portion and a second portion spaced from and parallel to the first portion. The fixture also includes the transverse edges of the first and second pair of face plates having an isolation portion interconnecting the first and second portions for isolating a portion of the weld which connects each of the planar blanks whereby the portion of the weld is isolated for shear strength testing in response to a tensile load being applied to the first and second pair of face plates.

The present invention further includes a method of testing the shear strength of a longitudinal weld interconnecting at least two planar blanks forming a tailor welded blank. The method includes the step of forming a cut slit through each of the planar blanks terminating at a portion of the weld. The method further includes the step of positioning the tailor welded blank between a first and second pair of face plates. The method includes the step of aligning a transverse edge of each of the first and second pair of face plates with the respective cut slit in each of the planar blanks and aligning an isolation portion of the transverse edge adjacent and parallel with the portion of the weld extending between the cut slits. The method also includes the step of securing the tailor welded blank between the first and second pair of face plates with the transverse edges extending across each of the planar blanks. Finally, the method includes the step of applying a tensile load to the first and second pair of face plates and the tailor welded blank to test the shear strength of the portion of the weld extending between the cut slits and isolated between the isolation portions of the transverse edges of the first and second pair of face plates.

One advantage of the present invention is that a fixture and method is provided for testing the shear strength in tailor welded blanks. Another advantage of the present invention is that the fixture and method provides an easy method of testing a tailor welded blank's resistance to shear loading and to quickly access the feasibility and formability of tailor welded blanks, particular for aluminum vehicle body structures.

Other features and advantages of the present invention will be readily appreciated as the same becomes better understood after reading the subsequent description when considered in connection with the accompanying drawings.

DESCRIPTION OF THE PREFERRED EMBODIMENT(S)

Figure 1:
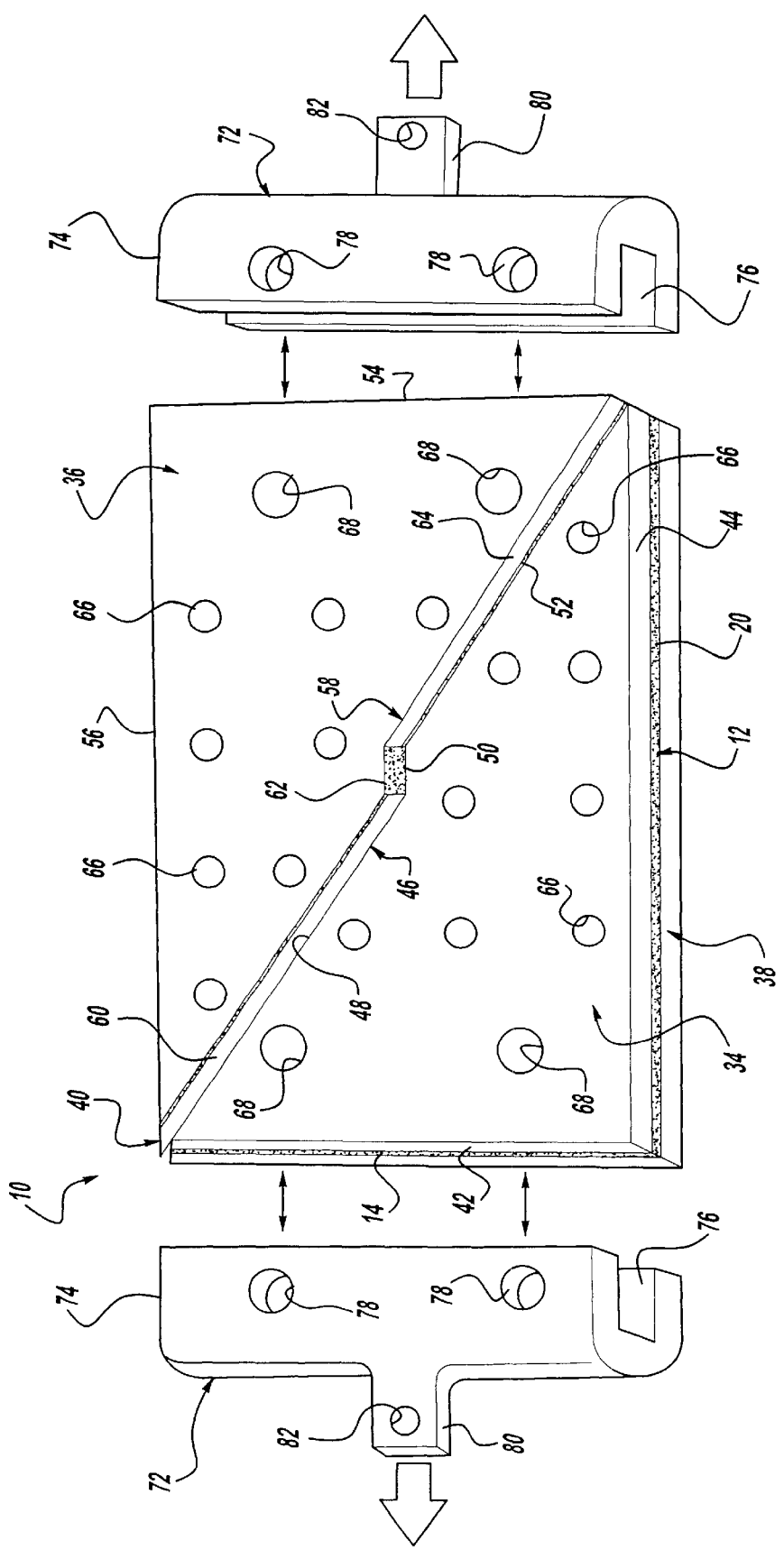
FIG. 1 is a partially exploded, perspective view of a fixture for testing the shear strength of a weld along a tailor welded blank, according to the present invention.
Figure 2:
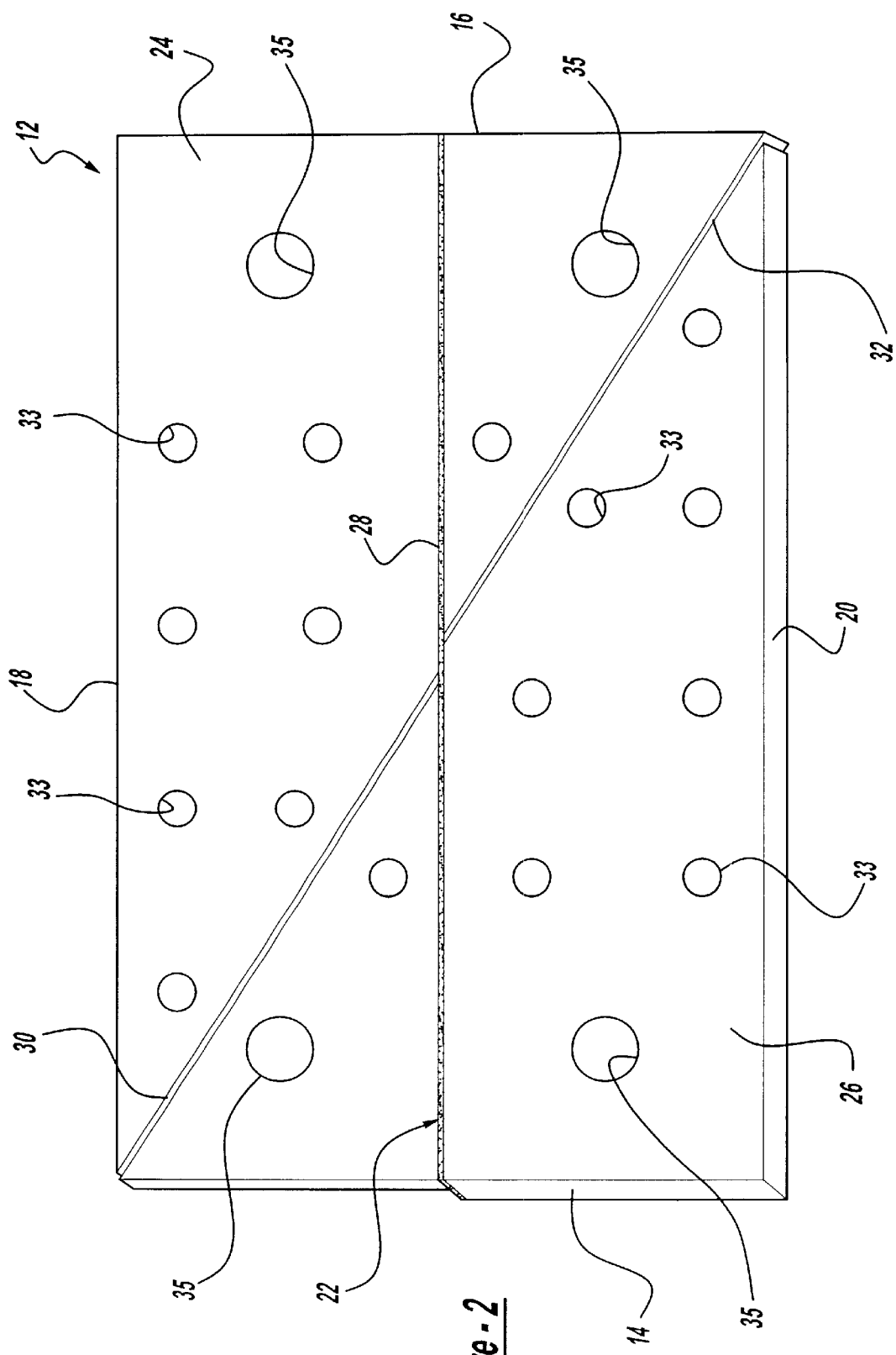
FIG. 2 is a perspective view of the tailor welded blank of FIG. 1.

Referring to the drawings and in particular FIG. 1, one embodiment of a fixture 10 for testing the shear strength of a generally longitudinal weld interconnecting at least two planar blanks, according to the present invention, is shown. As illustrated in FIGS. 1 and 2, a preformed tailor welded blank 12 for use as an automotive vehicle structure and adapted for testing of shear strength by the fixture 10 is shown. The tailor welded blank 12 is generally rectangular and includes a first end 14, a second end 16, a top edge 18, a bottom edge 20 and a center line 22 extending longitudinally between the first end 14 and the second end 18 approximately midway between the top edge 18 and the bottom edge 20. The tailor welded blank 12, in the preferred embodiment includes, two separate and planar first and second blanks 24, 26 of aluminum material having different thicknesses which are joined together along the center line 22 by a longitudinal weld 28. It should be appreciated that the tailor welded blank 12 may also include more than two planar blanks of different materials and thicknesses, each welded together to form the single tailor welded blank 12.

The tailor welded blank 12 further includes a pair of diagonally cut slits 30,32 extending from the circumferential edge of the tailor welded blank 12 to the longitudinal weld 28. More specifically, the first cut slit 30 extends diagonally from the corner of the first planar blank 24 defined by the intersection of the first end 14 and the top edge 18 to the weld 28 at a point approximately midway between the first end 14 and the second end 16. Similarly, the second cut slit 32 extends diagonally from the corner of the second planar blank 26 defined by the intersection of the second end 16 and the bottom edge 20 to the weld 28 at a point approximately midway between the first end 14 and the second end 16. The second cut slit 32 is spaced from and generally parallel to the first cut slit 30 as illustrated in FIG. 2. The area or section of the weld 28 between the first and second cut slits 30, 32 is therefore isolated from the remaining longitudinal sections of the weld 28. The tailor welded blank 12 also includes a plurality of fastening holes 33 extending there through and a pair of mounting holes 35 adjacent each of the first and second ends 14, 16 of the tailor welded blank 12 as will be described in greater detail herein below.

Figure 3:
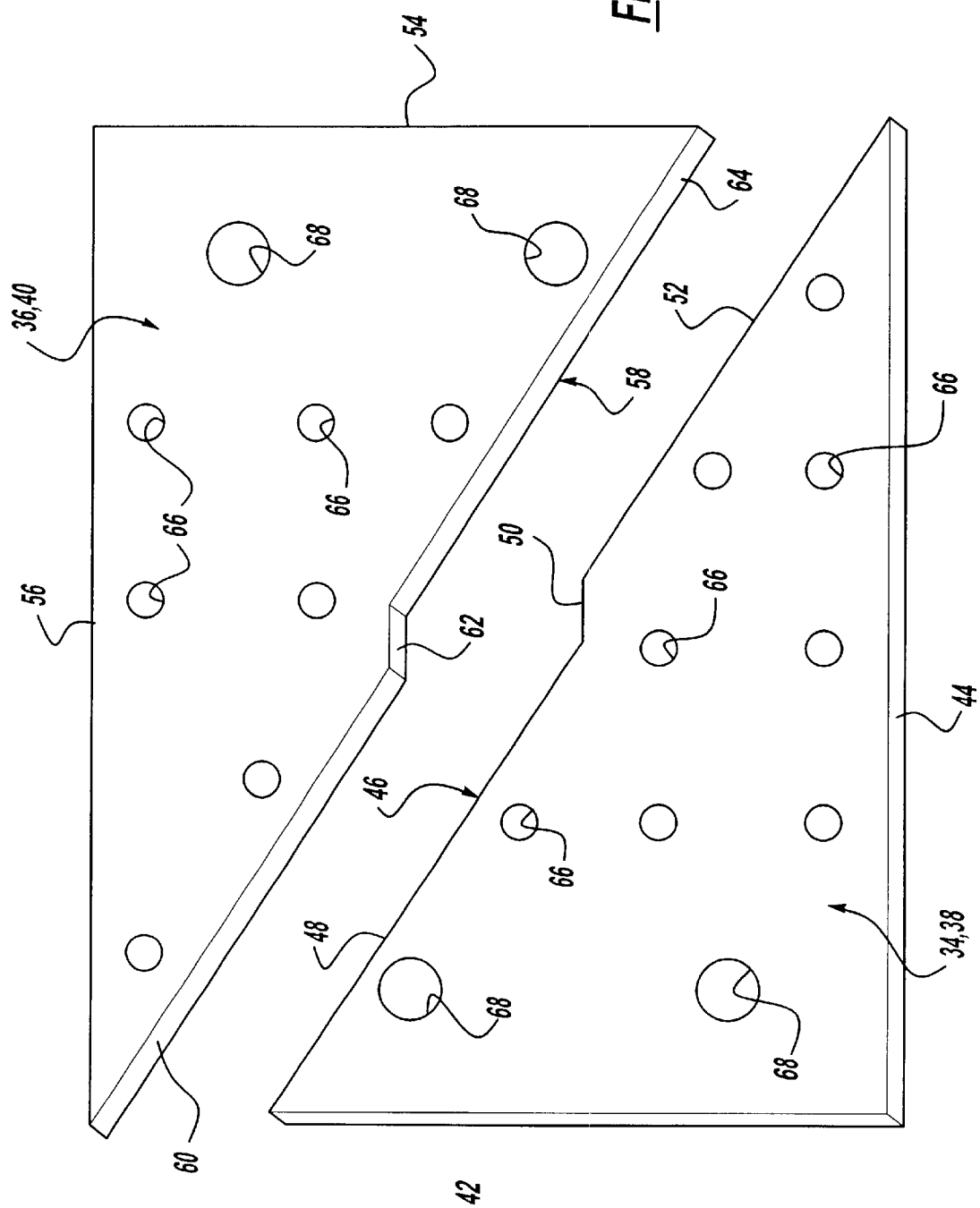
FIG. 3 is a perspective view of a first or second pair of face plates of the fixture of FIG. 1.

Referring now to FIGS. 1 and 3, the fixture 10 includes a first pair of face plates 34, 36 for attachment to one side of the tailor welded blank 12 and a second pair of face plates 38, 40 for attachment to the other side of the tailor welded blank 12 to form a sandwich-type configuration. The first pair of face plates 34, 36 include a lower face plate 34 having a generally triangular shape and an upper face plate 36 having a generally triangular shape substantially symmetrical to the lower face plate 34 as shown in FIGS. 1 and 3. Similarly, the second pair of face plates 38, 40 include a lower face plate 38 having a generally triangular shape and an upper face plate 40 having a generally triangular shape substantially symmetrical to the lower face plate 38. As illustrated in FIG. 1, the first pair of face plates 34, 36 are substantially identical to the second pair of face plates 38, 40, therefore, only the first pair of face plates 34, 36 will be described in greater detail. It should be appreciated that the second pair of face plates 38, 40 include the same configuration on the opposite side of the tailor welded blank 12.

The lower face plate 34 includes a lateral edge 42 for aligning with the first end 14 of the tailor welded blank 12 and a longitudinal edge 44 for aligning with the bottom edge 20 of the tailor welded blank 12. The lateral edge 42 and the longitudinal edge 44 are interconnected by a transverse edge 46 forming the generally triangular shaped lower face plate 34. The transverse edge 46 includes a first portion 48 extending from the lateral edge 42 to an isolation portion 50 and a second portion 52 extending from the isolation portion 50 to the longitudinal edge 44. The isolation portion 50 is generally parallel to the longitudinal edge 44 and positioned generally midway along the transverse edge 46 extending between the lateral edge 42 and the longitudinal edge 44.

Similarly, the upper face plate 36 includes a lateral edge 54 for aligning with the second end 16 of the tailor welded blank 12 and a longitudinal edge 56 for aligning with the top edge 18 of the tailor welded blank 12. The lateral edge 54 and the longitudinal edge 56 are interconnected by a transverse edge 58 forming the generally triangular shaped upper face plate 36. The transverse edge 58 includes a first portion 60 extending from the lateral edge 54 to an isolation portion 62 and a second portion 64 extending from the isolation portion 62 to the longitudinal edge 56. The isolation portion 62 is generally parallel to the longitudinal edge 56 and positioned generally midway along the transverse edge 58 extending between the lateral edge 54 and the longitudinal edge 56.

The first and second pair of face plates 34, 36, 38, 40 include a plurality of fastening holes 66 extending therethrough which align with the respective fastening holes 33 on the tailor welded blank 12 for securing the tailor welded blank 12 between the first pair of face plates 34,36 and the second pair of face plates 38, 40. Additionally, the first and second pair of face plates 34, 36, 38, 40 include a pair of mounting holes 68 extending therethrough which align with the respective mounting holes 35 on the tailor welded blank 12 for mounting the fixture 10 and the tailor welded blank 12 to a tensile testing machine (not shown, but commonly known in the art).

The tailor welded blank 12 is sandwiched and fastened between the first and second pair of face plates 34, 36, 38, 40 by securing a plurality of fasteners 70, such as bolts, through the respective fastening holes 33, 66. The face plates 34, 36, 38, 40 are aligned with respect to the tailor welded blank 12 such that the first portions 48, 60 of the transverse edges 46,58 are aligned with the first cut slit 30 of the tailor welded blank 12 and the second portions 52, 64 of the transverse edges 46, 58 are aligned with the second cut slit 32 of the tailor welded blank 12. The isolation portions 50, 62 provide a space or gap about a portion of the weld 28 to isolate the weld 28 for shear strength testing.

As illustrated in FIG. 1, the lower face plates 34, 38 are fastened about opposing sides of the tailor welded blank 12, both above and below the longitudinal weld 28, by the fastening holes 66 extending through a portion of both the first planar blank 24 and the second planar blank 26 adjacent the first end 14. Similarly, the upper face plates 36, 40 are also fastened about opposing sides of the tailor welded blank 12, both above and below the longitudinal weld 28, by the fastening holes 66 extending through a portion of both the first planar blank 24 and the second planar blank 26 adjacent the second end 16. The first and second cut slits 30, 32 and the transverse edges 46, 58 isolate the portion of the weld 28 aligned between the isolation portions 50, 62 of the face plates 34, 36, 38, 40.

The fixture 10 and the tailor welded blank 12 are mounted to the tensile testing machine (not shown) for testing the shear strength of the weld 28 by a pair of connectors 72 as illustrated in FIG. 1. The connector 72 is mounted by pins or bolts to the mounting holes 35, 68 adjacent each of the first and second ends 14, 16 for mounting the opposing longitudinal ends of the fixture 10 to the tensile testing machine (not shown). The connectors 72 include an elongated base portion 74 having a recessed slot 76 for receiving one of the opposing ends of the fixture 10 and tailor welded blank 12. A pair of bores 78 extend through the base portion 74 and slot 76 for aligning with the respective mounting holes 35, 68 in the fixture 10 and tailor welded blank 12 and receive pins or bolts therethrough to secure the connectors 72 to the opposing ends of the fixture 10. A connecting rod 80 extends outwardly from the base portion 74 and includes an aperture 82 for receiving a mounting fastener (not shown) for mounting the connectors 72 to the tensile testing machine (not shown).

In operation, the tailor welded blank 12 is first sandwiched and fastened between the first and second pair of face plates 34, 36, 38, 40 to isolate the portion of the weld 28 between the isolation portions 50, 62 of the first and second face plates 34, 36, 38, 40. The connectors 72 are mounted to the mounting holes 35, 68 on the fixture 10 and tailor welded blank 12 and the connectors 72 are mounted to the tensile testing machine (not shown). The fixture 10 tests the shear strength of the isolated portion of the weld 28 by applying a tensile force in opposing directions to the ends of the fixture 10 via the connectors 72 and tensile testing machine. The connectors 72 mounted to the pair of mounting holes 35, 68 prevent the fixture 10 from rotating under load and provide even load between the pair of first and second face plates 34, 36, 38, 40.

The present invention also includes a method of testing the shear strength of the longitudinal weld 28 which interconnects the upper and lower planar blanks 24, 26 forming the tailor welded blank 12. The method includes the steps of forming a cut slit 30, 32 through each of the planar blanks 24, 26, with the cut slits 30, 32 terminating at a portion of the weld 28. The method further includes the step of positioning the tailor welded blank 12 between the first and second pair of face plates 34, 36, 38, 40 and aligning the transverse edges 46, 58 of each of the first and second pair of face plates 34, 36, 38, 40 with the respective cut slit 30, 32 in each of the planar blanks 24, 26. The method includes the step of aligning the isolation portions 50, 62 of the transverse edges 46, 58 adjacent to and parallel with the portion of the weld 28 extending between the cut slits 30, 32. The method then includes securing the tailor welded blank 12 between the first and second pair of face plates 34, 36, 38, 40 with the transverse edges 46, 58 extending across each of the planar blanks 24, 26 and weld 28. Finally, the method includes the step of applying a tensile load to the first and second pair of face plates 34, 36, 38, 40 and the tailor welded blank 12 to test the shear strength of the portion of the weld 28 extending between the cut slits 30, 32 and isolated between the isolation portions 50, 62 of the face plates 34, 36, 38, 40.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A fixture for testing shear strength of a generally longitudinal weld interconnecting at least two planar blanks forming a tailor welded blank, said fixture comprising:
   a first pair of face plates for connection to one side of the planar blanks, each of said first pair of face plates including a transverse edge adapted to extend across the longitudinal weld connecting each of the planar blanks;
   a second pair of face plates for connection to the opposing side of the planar blanks, each of said second pair of face plates including a transverse edge adapted to extend across the longitudinal weld connecting each of the planar blanks;
   each of said transverse edges of said first and second pair of face plates including a first portion and a second portion spaced from and parallel to said first portion; and
   each of said transverse edges of said first and second pair of face plates including an isolation portion interconnecting said first portion and said second portion for isolating a portion of the weld connecting each of the planar blanks, whereby the portion of the longitudinal weld is isolated for shear strength testing in response to a tensile load applied to the first and second pair of face plates.

2. A fixture as set forth in claim 1 wherein each of said first and second pair of face plates include a lower face plate and an upper face plate, said transverse edge of said lower face plate being aligned in mating relationship with said transverse edge of said upper face plate.

3. A fixture as set forth in claim 2 wherein each of said lower face plate and said upper face plate include a lateral edge and a longitudinal edge, said first portion of said transverse edge extending from said lateral edge to said isolation portion and said second portion of said transverse edge extending from said isolation portion to said longitudinal edge.

4. A fixture as set forth in claim 3 wherein said first portion of said transverse edge is laterally spaced from and parallel to said second portion of said transverse edge, said isolation portion interconnecting said first and second portions between said lateral edge and said longitudinal edge.

5. A fixture as set forth in claim 4 wherein each of said upper face plate and said lower face plate includes a plurality of fastening holes extending therethrough for interconnecting said first and second pair of face plates about the tailor welded blank.

6. A fixture as set forth in claim 5 wherein each of said upper face plate and said lower face plate includes a pair of mounting holes for mounting said fixture to a tensile testing machine.

7. A fixture as set forth in claim 6 further including a connector for attaching to said mounting holes on said fixture and mounting said lateral edges of said upper face plate and said lower plate to the tensile testing machine.

8. A method of testing shear strength of a longitudinal weld interconnecting at least two planar blanks forming a tailor welded blank, said method comprising the steps of:
   forming a cut slit through each of the planar blanks terminating at a portion of the weld;
   positioning the tailor welded blank between a first and second pair of face plates;
   aligning a transverse edge of each of the first and second pair of face plates with a respective cut slit in each of the planar blanks;
   aligning an isolation portion of the transverse edge adjacent and parallel with the portion of the weld extending between the cut slits;
   securing the tailor welded blank between the first and second pair of face plates with the transverse edges extending across each of the planar blanks; and
   applying a tensile load to the first and second pair of face plates and the tailor welded blank to test the shear strength of the portion of the weld extending between the cut slits and isolated between the isolation portions of the transverse edges of the face plates.

9. A fixture for testing shear strength of a generally longitudinal weld interconnecting at least two planar blanks forming a tailor welded blank, said fixture comprising:
   a first pair of face plates for connection to one side of the planar blanks, each of said first pair of face plates including a transverse edge adapted to extend across the longitudinal weld connecting each of the planar blanks;
   a second pair of face plates for connection to the opposing side of the planar blanks, each of said second pair of face plates including a transverse edge adapted to extend across the longitudinal weld connecting each of the planar blanks, each of said first pair of face plates and said second pair of face plates including a plurality of fastening holes extending therethrough for receiving fasteners for interconnecting said first pair of face plates and said second pair of face plates about the tailor welded blank;

each of said transverse edges of said first and second pair of face plates including a first portion and a second portion spaced from and parallel to said first portion; and each of said transverse edges of said first and second pair of face plates including an isolation portion interconnecting said first portion and said second portion for isolating a portion of the weld connecting each of the planar blanks, whereby the portion of the longitudinal weld is isolated for shear strength testing in response to a tensile load applied to the first and second pair of face plates.

* * * * *